(12) United States Patent
Turnbull

(10) Patent No.: US 6,742,519 B2  
(45) Date of Patent: Jun. 1, 2004

(54) MEDICO-SURGICAL APPARATUS

(75) Inventor: Christopher Stratton Turnbull, Hythe (GB)

(73) Assignee: Smiths Group PLC, London (GB)

(*) Notice: Subject to any disclaimer, the term of this patent is extended or adjusted under 35 U.S.C. 154(b) by 0 days.

(21) Appl. No.: 10/334,907

(22) Filed: Jan. 2, 2003

(65) Prior Publication Data

US 2003/0136414 A1 Jul. 24, 2003

(30) Foreign Application Priority Data

Jan. 23, 2002 (GB) .............................................. 0201436

(51) Int. Cl.⁷ .............................................. A61M 16/00
(52) U.S. Cl. .............................. 128/207.29; 128/207.14
(58) Field of Search ................. 128/207.29, 207.14, 128/200.26, 207.15; 606/191, 192, 194, 108, 198; 604/96.01, 160, 161, 264, 272

(56) References Cited

U.S. PATENT DOCUMENTS

| | | | |
|---|---|---|---|
| 3,613,684 A | 10/1971 | Sheridan | |
| 3,916,903 A * | 11/1975 | Pozzi | 128/207.29 |
| 3,991,765 A * | 11/1976 | Cohen | 128/207.29 |
| 4,565,544 A | 1/1986 | Muller et al. | |
| 4,877,021 A * | 10/1989 | Higer et al. | 128/200.26 |
| 5,055,107 A * | 10/1991 | Lester | 604/540 |
| 5,058,580 A * | 10/1991 | Hazard | 128/207.15 |
| 5,297,546 A * | 3/1994 | Spofford et al. | 128/207.14 |
| 5,320,608 A | 6/1994 | Gerrone | |
| 5,364,367 A | 11/1994 | Banks et al. | |
| 5,507,279 A * | 4/1996 | Fortune et al. | 128/200.26 |
| 5,546,939 A * | 8/1996 | French | 128/207.29 |
| 5,653,230 A * | 8/1997 | Ciaglia et al. | 128/207.15 |
| 5,967,143 A * | 10/1999 | Klappenberger | 128/207.29 |
| 6,109,264 A * | 8/2000 | Sauer | 128/207.29 |
| 6,298,851 B1 * | 10/2001 | Parota et al. | 128/207.29 |
| 6,637,435 B2 * | 10/2003 | Ciaglia et al. | 128/207.29 |

FOREIGN PATENT DOCUMENTS

GB 1459741 12/1976

* cited by examiner

*Primary Examiner*—Henry Bennett  
*Assistant Examiner*—Teena Mitchell  
(74) *Attorney, Agent, or Firm*—Louis Woo

(57) ABSTRACT

A percutaneous tracheostomy assembly has a hollow needle carrying a cannula with a hub at its rear end abutting a hub on the needle. A channel-shape stop is clipped onto the cannula and needle so that its rear end abuts the hub of the cannula. The stop has a laterally-extending flange at its forward end. The length of the stop is such that the tip of the needle and the forward end of the cannula are positioned within the trachea when the flange abuts the skin of the neck, without the risk of the needle contacting the posterior wall of the trachea.

13 Claims, 1 Drawing Sheet

MEDICO-SURGICAL APPARATUS

BACKGROUND OF THE INVENTION

This invention relates to medico-surgical apparatus.

One technique for performing a percutaneous tracheostomy involves a needle carrying a cannula. An initial cut is made with a scalpel through the skin of the neck and the needle is pushed through neck tissues and the anterior wall of the trachea so that the tip of the needle and the cannula locate in the trachea. The needle is then pulled out to leave the cannula in place. A guidewire is inserted through the cannula, which is then removed. A dilator is slid along the guidewire to expand the opening through the tissue sufficiently to receive a tracheostomy tube. The dilator may take various forms, such as an expanding forceps, as described in EP0505390, or a tapering dilator or series of tapering dilators.

One problem with this technique is that, the needle must be sufficiently long to accommodate the cannula, making it long enough to contact the posterior wall of the trachea. This can lead to damage to the wall of the trachea if used incorrectly. In extreme cases, the needle could be pushed through the posterior wall of the trachea into the oesophagus, causing the guidewire and dilators to be inserted in the oesophagus.

BRIEF SUMMARY OF THE INVENTION

It is an object of the present invention to provide alternative medico-surgical apparatus.

According to one aspect of the present invention there is provided a tracheostomy assembly including a needle having a pointed first end adapted for insertion through neck tissue into the trachea, a cannula extending along the outside of the needle and a stop mounted on the cannula, the stop having a first end adapted to limit the extent of insertion of the assembly in the trachea, and the stop being removable from the cannula when the cannula is located in the trachea.

The stop is preferably a clip-fit on the cannula and is removable laterally. The stop is preferably of channel shape. The cannula may have an enlarged portion towards its rear end, the stop being adapted to engage the enlarged portion. The enlarged portion is preferably a hub. The needle preferably has an enlarged portion towards its rear end, which may be a hub. The first end of the stop is preferably spaced rearwardly of the first end of the needle by substantially 20 mm. The stop may have a laterally extending flange at its first end. The stop may be held on the cannula by resilience of the stop.

According to another aspect of the invention there is provided a stop for a tracheostomy assembly according to the above one aspect of the invention.

A percutaneous tracheostomy assembly according to the present invention, will now be described, by way of example, with reference to the accompanying drawing.

DETAILED DESCRIPTION OF THE PREFERRED EMBODIMENT

Figure 1:
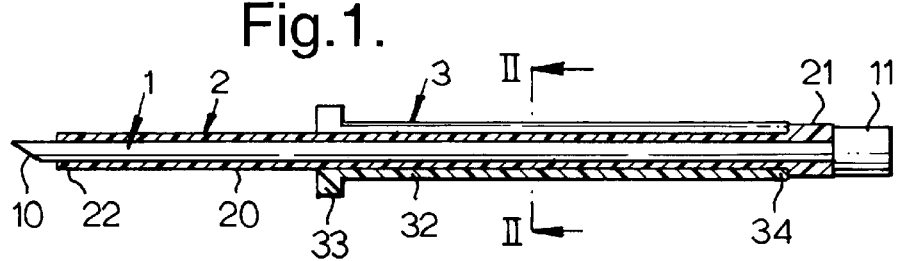
FIG. 1 is a cross-sectional side elevation view of the assembly.
Figure 2:
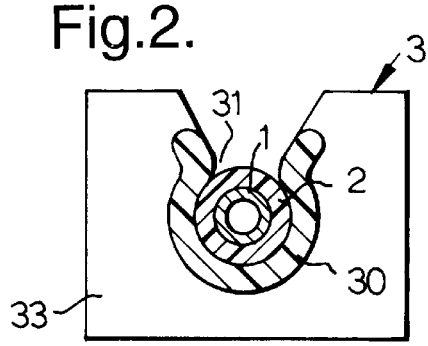
FIG. 2 is an enlarged transverse sectional view of the assembly along the line II—II of FIG. 1.
Figure 3:
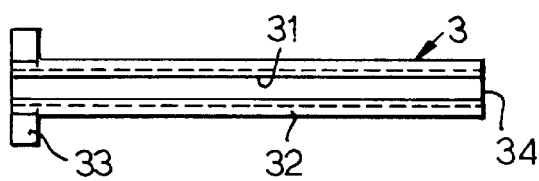
FIG. 3 is a plan view of the stop.

With reference first to FIGS. 1 to 3, the assembly includes a needle 1, a cannula 2 and a stop 3.

The needle 1 is hollow and of metal, with a pointed penetrating tip 10 at one end and an enlarged moulded hub 11 at its opposite end.

The cannula 2 is of plastics material having a flexible shaft 20 and an enlarged hub 21 at its rear end. The cannula 2 is a close sliding fit on the needle 1 with its hub 21 located against the hub 11 of the needle and with its forward end 22 located just rearwardly of the tip 10 of the needle.

The stop 3 is moulded from a relatively hard plastics material and comprises a channel portion 30 of generally omega shape in section with an open upper surface provided by a flared entrance portion 31. The main part 32 of the channel 30 has a substantially circular section with an internal diameter equal to the external diameter of the cannula 2. The entrance portion 31 has a width at its narrowest part that is less than the diameter of the cannula 2. The channel 30 acts as a resilient clip to retain the stop 3 on the cannula 2. At its forward, patient end, the stop 3 has a laterally-extending flange 33, which acts to limit the extent of insertion of the assembly. The stop 3 is clipped onto the cannula 2 and needle 1 laterally from one side with its rear end 34 abutting the hub 21 on the cannula. The length of the stop 3 is selected so that, when fitted on the cannula and needle, about 20 mm of needle protrudes beyond the flange 33 at the forward end of the stop. This is insufficient to allow the tip 10 of the needle 1 to contact or penetrate the posterior wall of the trachea.

Figure 4:
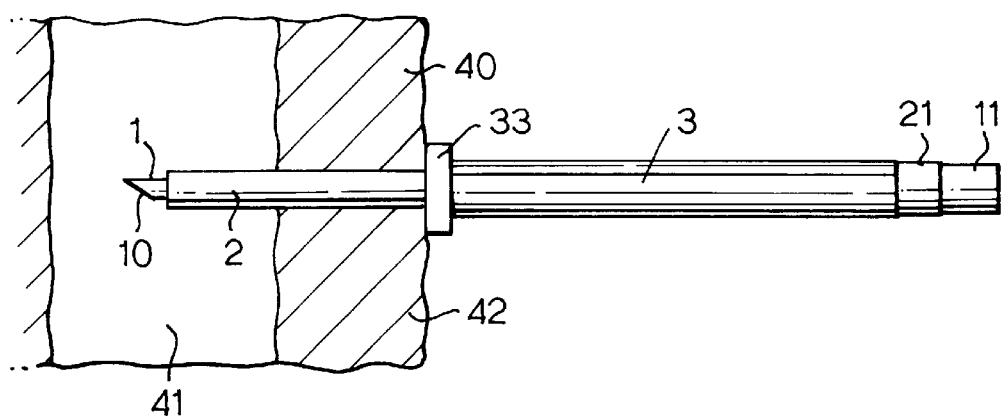
FIG. 4 is a partly sectional side elevation view showing the assembly in use.

As shown in FIG. 4, when the assembly is pushed through neck tissue 40 into the trachea 41, the extent of insertion is limited by abutment of the flange 33 on the stop 3 with the skin 42. The stop 3 is then unclipped from the cannula 2 by pulling it laterally. The needle 1 is then slid out and a guidewire (not shown) is inserted along the cannula 2 in the usual way so that dilators can, in turn be slid along the guidewire to enlarge the opening into the trachea. It will be appreciated that the stop could have other constructions enabling it to be removed from the cannula and needle while the forward, patient end of the cannula is located in the trachea.

The stop and assembly of the present invention enables a conventional percutaneous needle and cannula to be used with a reduced risk of injury to the patient.

What I claim is:

1. A tracheostomy assembly comprising: a needle, said needle having a pointed first end adapted for insertion through neck tissue into the trachea; a cannula extending along an outside of said needle; and a stop mounted on said cannula, wherein said stop has a first end adapted to abut a surface of the neck and thereby limit the extent of insertion of the assembly in the trachea, and wherein said stop is removably laterally from said cannula when said cannula is located in the trachea.

2. A tracheostomy assembly according to claim 1, wherein said stop is a clip fit on said cannula.

3. A tracheostomy assembly according to claim 1, wherein said stop is of channel shape.

4. A tracheostomy assembly according to claim 1, wherein said cannula has an enlarged portion towards its rear end, and wherein said stop is adapted to engage said enlarged portion.

5. A tracheostomy assembly according to claim 4, wherein said enlarged portion is a hub.

6. A tracheostomy assembly according to claim 1, wherein said needle has an enlarged portion towards its rear end.

7. A tracheostomy assembly according to claim 6, wherein said enlarged portion on said needle is a hub.

8. A tracheostomy assembly according to claim 1, wherein said first end of said stop is spaced rearwardly of said first end of said needle by substantially 20 mm.

9. A tracheostomy assembly according to claim 1, wherein said stop has a laterally extending flange at its first end.

10. A tracheostomy assembly according to claim 1, wherein said stop is held on said cannula by resilience of said stop.

11. A tracheostomy assembly comprising: a needle, said needle having a pointed first end adapted for insertion through neck tissue into the trachea; a cannula extending along an outside of said needle; and a resilient channel shape clip fastened about said cannula and said needle, wherein said clip has an enlarged first end adapted to limit the extent of insertion of the assembly in the trachea, and wherein said clip is removable laterally from said cannula and said needle.

12. A tracheostomy assembly according to claim 11, wherein said needle has an enlarged hub at a second end opposite said first end, wherein said cannula has an enlarged hub at a second end opposite said first end, wherein a second end of said clip opposite said first end engages the hub of said cannula, and wherein the hub of said cannula engages the hub of said needle.

13. A method of performing a tracheostomy comprising the steps of:

providing an assembly of a needle, said needle having a pointed first end; a cannula extending along an outside of said needle, said cannula having a first end and a second end; and a stop mounted on said cannula, said stop having a first end and a second end;

inserting the first end of said needle and said cannula through neck tissue into the trachea until said first end of said stop abuts neck tissue;

removing said needle; and removing said stop laterally from said cannula to leave said cannula in position in the trachea.

\* \* \* \* \*